United States Patent

Procter et al.

[11] Patent Number: 5,527,311
[45] Date of Patent: Jun. 18, 1996

[54] SUPPORT FOR THE HUMAN SPINE

[75] Inventors: Philip Procter, Surrey, Great Britain; Hans E. Harder, Probsteierhagen, Germany; Nicola Bird, South Bucks, Great Britain

[73] Assignee: Howmedica GmbH, Schoenkirchen, Germany

[21] Appl. No.: 282,700

[22] Filed: Jul. 29, 1994

Related U.S. Application Data

[63] Continuation of Ser. No. 972,705, Nov. 6, 1992, abandoned.

[30] Foreign Application Priority Data

Nov. 13, 1991 [DE] Germany .............. 9114118 U

[51] Int. Cl.⁶ ...................................... A61B 17/70
[52] U.S. Cl. ............................. 606/61; 606/69
[58] Field of Search ............... 606/61, 69, 70, 606/71, 72, 73; 623/17

[56] References Cited

U.S. PATENT DOCUMENTS

| | | | |
|---|---|---|---|
| 1,105,105 | 7/1914 | Sherman | 606/69 |
| 2,580,821 | 1/1952 | Nicola | 606/69 |
| 2,980,110 | 4/1961 | Brumfield et al. | |
| 3,716,050 | 2/1973 | Johnston | 606/69 |
| 3,741,205 | 6/1973 | Markoff et al. | 606/61 |
| 3,779,240 | 12/1973 | Kondo | 606/69 |
| 4,493,317 | 1/1985 | Klaue | 606/69 |
| 4,696,290 | 9/1987 | Steffee | 128/69 |
| 5,015,248 | 5/1991 | Burstein et al. | 606/74 |
| 5,147,361 | 9/1992 | Ojima et al. | 606/61 |
| 5,180,381 | 1/1993 | Aust et al. | 606/61 |
| 5,201,737 | 4/1993 | Leibinger et al. | 606/69 |

FOREIGN PATENT DOCUMENTS

| | | | |
|---|---|---|---|
| 0290138 | 11/1988 | European Pat. Off. | |
| 0410309 | 7/1990 | European Pat. Off. | |
| 2405706 | 5/1979 | France | |
| 549079 | 4/1932 | Germany | 606/69 |
| 611147 | 5/1979 | Switzerland | |
| 569307 | 8/1977 | U.S.S.R. | 606/69 |
| 2125295 | 3/1984 | United Kingdom | |
| 9004366 | 5/1990 | WIPO | |
| 9013266 | 11/1990 | WIPO | |
| 9211819 | 7/1992 | WIPO | |

OTHER PUBLICATIONS

Uza Nudell, "Stainless Steel Skull Plate" Annals of Surgery, Jul. 1948, p. 33.

*Primary Examiner*—Stephen C. Pellegrino
*Assistant Examiner*—Guy Tucker
*Attorney, Agent, or Firm*—Peter C. Richardson; Lawrence C. Akers; Elizabeth O. Slade

[57] ABSTRACT

The invention is an elongated plate made of deformable, body-compatible material, which is to be anteriorly attached to at least a pair of adjacent vertebrae. The plate has specially placed holes to receive bone screws to be screwed into the vertebrae.

4 Claims, 1 Drawing Sheet

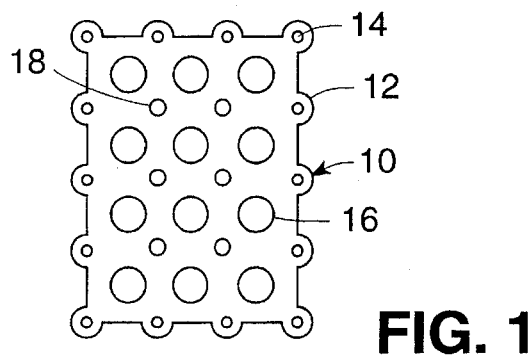
FIG. 1
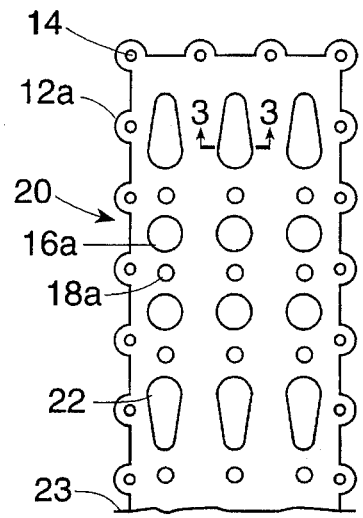
FIG. 2
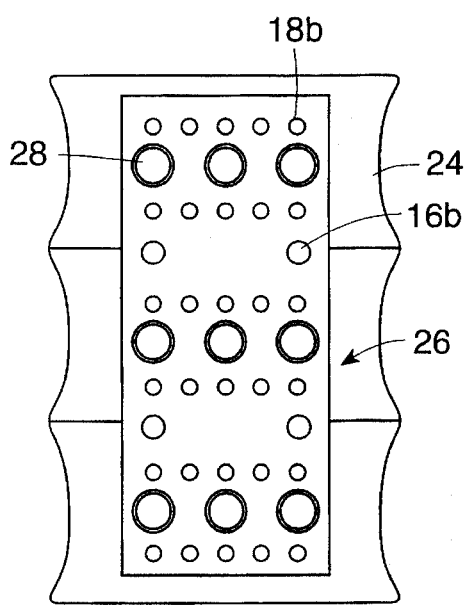
FIG. 4
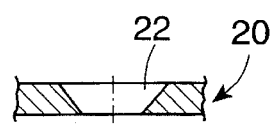
FIG. 3
FIG. 5
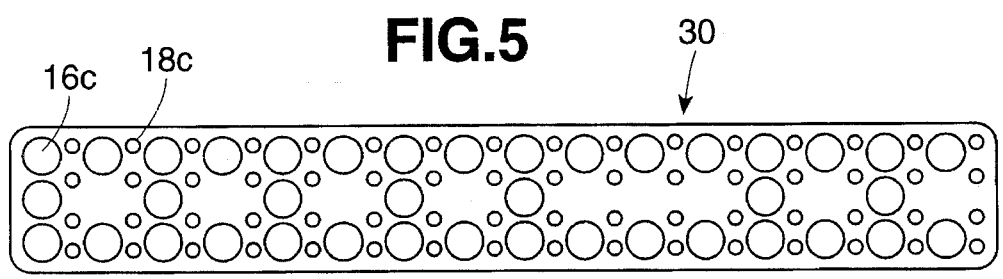

SUPPORT FOR THE HUMAN SPINE

This is a continuation of application Ser. No. 07/972,705, filed on Nov. 6, 1992 now abandoned.

FIELD OF THE INVENTION

The present invention relates to a sustaining means for correcting and/or stabilizing injured or deficient vertebras of the human spine according to the preamble of claim 1.

DESCRIPTION OF RELATED ART

German petty patent 87 11 317 discloses so-called Schanz screws which are screwed in the vertebra through the pedicels to reposition healthy and/or fractured vertebras. The Schanz screws are secured to a sustaining means which provides an adjustment of the Schanz screws with respect to all three degrees of freedom. The known sustaining means, however, are not able to bridge more than a vertebra or to provide for a multi-segmental treatment of multiple fractures. To provide for an implantation, the Schanz screws must be cut off after securing to the sustaining means. Consequently, burs are formed at the end of the screws. Due to the need of substantial space, the known sustaining means may not be used in the upper range of the spine, in particular in the cervical vertebra zone.

SUMMARY OF THE INVENTION

A number of vertebras may be bridged by a so-called Harrington rod to which hooks or pedicel screws are attached. However, a Harrington rod cannot be individually adjusted to the particular shape of the spine in the zone where it is applied. Therefore, it has been known to use a threaded wire cooperating with pedicel screws. This known sustaining means, however, does not provide a primary stable support because it exhibits non-sufficient strength. Therefore it can be used mainly for spines which are stable per se and of which the course has to be corrected for orthopedic reasons.

German petty patent 88 02 112 discloses a sustaining means for the human spine, wherein between adjacent pedicel screws a tension Jack is provided which ends include clamping faces for clamping to the head of a pedicel screw. By adjusting the axial distance of the belts with respect to each other, for example by means of a threaded sleeve, the attachment points of the pedicel screws may be adjusted. Still further the bolts provide for a rotation of the pedicel screws about the bolt axis at a desired angle. Furthermore, the pedicel screws may be pivoted about an axis normal to the axis with respect to the attachment points to be fixed in a desired position. The pedicel screw may thus take any desired position in space and can be fixed in this position. The known sustaining means provides for screwing pedicel screws into each desired vertebra to fix desired vertebras of a spine portion with respect to each other. The sustaining means described is thus suited to primarily stabilize the spine, when one or more vertebras are fractured. However, even this sustaining means which is dorsally implanted, which means a relatively small stress to the patient is not suited to be used for the upper spine zone, in particular for the cervical vertebras.

Accordingly, the invention is based on the object to provide a sustaining means for the correction and/or stabilization of injured or deficient vertebras of the human spine, which may be used in the upper zone of the spine.

The object referred to is solved by the features of claim 1.

According to the invention the sustaining means consists of an elongated plate made of deformable, body-compatible material, which is anteriorly attached to at least a pair of adjacent vertebras. The plate comprises holes to receive bone screws to be screwed in the vertebrae. The plate further comprises weakening zones and/or thickness dimensions and/or a selection of material such that it may be adjusted to the contour of the vertebras.

According to the invention the plate is suited to be pre-shaped before the operation to conform to the contour of the vertebras or to be shaped by the surgeon right during the operation. Thereafter, the plate is fixed by bone screws to the vertebras whereby screw holes are formed substantially in the center axis of the plate and additionally towards the edge which is bent in the longitudinal axis to fit to the vertebra. To fit the plate to the depressions in the vertebra, the plate is further bent around a normal axis so that the plate obtains a substantial stability due to the different bending which stability is sufficient for a primary setting of fractured or deficient vertebras, for example.

Attaching the plate is performed anterior, i.e. from the front side so that it is particularly suited for the cervical vertebras of the spine. The attachment does not involve particular problems and needs extremely little space thus being less detrimental to the patient. The bone screws are either anchored in the vertebra only or additionally in the pedicels of the vertebras or in the pedicels exclusively.

The plate of the invention must represent a sufficient deformability on the one hand and a sufficient stiffness on the other. According to the invention a weakening of the plate to facilitate deformability is provided by a plurality of preferrably round holes having a diameter which is smaller than the diameter of the screw holes. A weakening of this type is relatively easy to manufacture. Therefore, a further embodiment of the invention provides to arrange the screw holes or the weakening zones of the plate and thus of the smaller holes such that the plate is stiffer in its central longitudinal zone than towards the longitudinal edge. Therefore, the plate may be more easily deformed along the length edge than towards the central portion which feature facilitates fitting the plate to the contour of the vertebras.

To prevent weakening the plate too much, the number of holes should be limited. According to an embodiment of the invention, the distance or the multiple of the distance of the screw holes in the length axis of the plate substantially corresponds to the center distance of adjacent vertebras, possibly taking into account the shaping along a normal axis or length axis to fit to the contour of the vertebras. Particularly in the cervical vertebra range the bone screws are more easily screwed centrally in the vertebra than in the lower or upper range.

The length of the plate depends on the size of the injured range. Possibly a plate covering two vertebras is sufficient. However, as the case may be, the length of the plate may be selected substantially larger. To prevent preparing an individual plate for each length, the invention provides for an endless plate which may be cut. Thus, the surgeon may determine the length of the plate which is cut from a suitable stock.

According to a further embodiment of the invention the screw holes in the end areas of the plate are elongated tapering towards the end thereof to become more narrow and the edges of the holes are sloped to cooperate with the conical underside of the screw head. In this way a compression force may be created when the conical undersides of the screw heads cooperate with the elongate holes.

A further embodiment of the invention provides ear-like projections along the edges of the plate including small holes. The holes may accomodate wires, for example to obtain an additional fixing.

BRIEF DESCRIPTION OF THE DRAWING

Various embodiments of the invention are described in more details in referring to the drawings.

FIG. 1 a top view of a first embodiment of a schematically illustrated plate according to the invention, FIG. 2 show a top view of a second embodiment of the invention, FIG. 3 shows a section through FIG. 2 along lines 3—3, FIG. 4 shows a top view of a third embodiment of the invention and FIG. 5 shows a top view of a fourth embodiment of a plate according to the invention.

DESCRIPTION OF THE PREFERRED EMBODIMENTS

FIG. 1 shows a plate 10 made of flat material of a body-compatible material, for example titane. Along the edges and at the corners the plate 10 comprises small ear-like projections 12 including including small circular holes 14. The plate 10 further comprises four lines of screw holes 16 to receive bone screws. Smaller circular holes 18 are formed between the screw holes 16. The distance of the screw holes 16 in the lines approximately corresponds to the central distance of adjacent cervical vertebras, for example. By the individual holes and/or the selection of material, the plate 10 is suited to more or less closely fit to the contour of cervical vertebras. The shaping may be performed before the operation or during the operation. By means of bone screws not shown the plate 10 is then fixed to adjacent vertebras, wherein a part only of the screw holes is used. A wire used for an additional fixing may be pulled through the holes 14 in the ear-like projection 12.

The plate 20 of FIG. 2 is of similar structure as the plate 10 of FIG. 1. Alike, it comprises ear-like projections 12a including holes 14a and lines of screw holes 16a and smaller holes 18a therebetween. Furthermore, elongated holes 22 are provided in a predetermined distance, which are narrowed towards the end of plate 20. The edge of the holes 22 is conical, as FIG. 3 shows so that by means of a conical screw head a compression may be exerted on the vertebra in which the screw in the elongated holes 22 are screwed in. The plates 20 may be made of an endless material as indicated at 23 and from this material a desired length is cut off, in particular by the surgeon.

FIG. 4 shows vertebras 24 of cervical vertebras which are connected to each other by a plate 26. The structure of the plate 26 corresponds to the plate 10 of FIG. 1, i.e. the plate comprises rows of screw holes 16b and rows of holes 18b having a smaller diameter to facilitate shaping. The plate 26 is bent along its length axis, in particular in the edge zone and in addition thereto along its normal axes to better fit to the outer contour of the vertebras 24. Only the screw holes 16b located in the center of the vertebras 24 accomodate bone screws 28.

The plate 30 shown in FIG. 5 is provided with rows of screw holes 16c wherein rows with three screw holes 16c alternate with rows of two screw holes 16c. The distance between the rows with three screw holes 16c or, respectively between the rows with two screw holes 16c approximately corresponds again to the center distance of adjacent vertebras of the cervical spine. Between the screw holes, rows of through holes 18c of smaller diameter are provided. One realizes, that by providing the screw holes 16c, the plate 30 is stiffer in its central region than towards the longitudinal edges. This is augmented by selecting the distance of both the central holes 18c larger than between a central and an outer hole 18c of the row. Thus, a relatively high ductibility is obtained in the edge zone, whereas the central region is substantially stiffer.

Preferably, the plate 30c is made endless so that the surgeon cuts off a suitable length.

We claim:

1. A spinal support plate for attachment to at least a pair of adjacent vertebrae of the spine, said plate having a longitudinal axis adapted to be parallel to the longitudinal axis of the spine when the plate is attached to adjacent vertebrae, said plate comprising:

at least three rows of three holes each for receiving bone screws of a predetermined diameter, each of said rows aligned along an axis perpendicular to said longitudinal axis of said spinal support plate; and at least two additional rows of at least two smaller diameter holes each, said holes in said additional rows having a diameter smaller than said predetermined diameter and smaller than the diameter of said holes for receiving said bone screws, said rows aligned along an axis perpendicular to said longitudinal axis of said spinal support plate, said at least two rows of smaller diameter holes located between adjacent rows of said holes for receiving said bone screws.

2. A support plate according to claim 1 wherein one of said screw holes in each row is located substantially along said longitudinal axis, said one of said screw holes in each row being spaced apart at a distance which corresponds substantially to the distance between adjacent vertebrae.

3. A support plate as set forth in clam 1 wherein ear-like projections extend from the edges of said plate, said projections including holes, said holes aligned with said axis of said rows of smaller diameter holes.

4. A support plate as set forth in claim 1 wherein one of said bone screw receiving holes in each row is located on said longitudinal axis.

* * * * *